United States Patent [19]
van der Wal

[11] Patent Number: 5,569,192
[45] Date of Patent: Oct. 29, 1996

[54] AUTOMATIC INJECTOR

[75] Inventor: Gillis P. van der Wal, Olst, Netherlands

[73] Assignee: Duphar International Research B.V., Weesp, Netherlands

[21] Appl. No.: 36,373

[22] Filed: Mar. 24, 1993

[30] Foreign Application Priority Data

Mar. 27, 1992 [EP] European Pat. Off. ............ 92200877

[51] Int. Cl.$^6$ ................................................ A61M 37/00
[52] U.S. Cl. .............................. 604/84; 604/87; 604/89; 604/135
[58] Field of Search .................. 604/130, 134–139, 604/156–157, 188, 191, 197–198, 82, 84, 85–89, 90–92, 148, 143, 144, 194, 199, 195, 231, 221–222, 183, 184

[56] References Cited

U.S. PATENT DOCUMENTS

| | | | |
|---|---|---|---|
| 2,228,537 | 1/1941 | Smith | 604/91 |
| 4,755,169 | 7/1988 | Sarnoff et al. | |
| 4,820,286 | 4/1989 | van der Wal | 604/89 |
| 4,822,340 | 4/1989 | Kamstra | |
| 4,968,302 | 11/1990 | Schluter et al. | 604/135 |
| 4,983,164 | 1/1991 | Hook et al. | 604/87 |
| 5,041,088 | 8/1991 | Ritson et al. | |

*Primary Examiner*—Randall L. Green
*Assistant Examiner*—V. Alexander
*Attorney, Agent, or Firm*—Watson Cole Stevens Davis, P.L.L.C.

[57] ABSTRACT

An automatic injector for the separate storage of a solid and a solvent for this solid. The injector comprises a discharge mechanism, a cartridge assembly and a front cover which is connected to a front portion of the cartridge assembly and provided at its front with a pierceable central area. The cartridge assembly comprises a hollow barrel, a pierceable stopper connected to the front portion of the barrel and constituting a compartment in front of said stopper for accommodating the solid, a piston slidably accommodated in the backward portion of the barrel and constituting a compartment for liquid in the barrel, an injection needle longitudinally extending in the liquid compartment, and means for centering the distal end of the needle in order to position the needle tip towards the pierceable stopper. The front cover is capable of rotational movement relative to the outer sleeve to allow the liquid in the barrel to reach the solid compartment through the needle. The injection needle is accommodated in the barrel in an unfixed manner to allow relative longitudinal movement between the injection needle and the barrel.

12 Claims, 7 Drawing Sheets

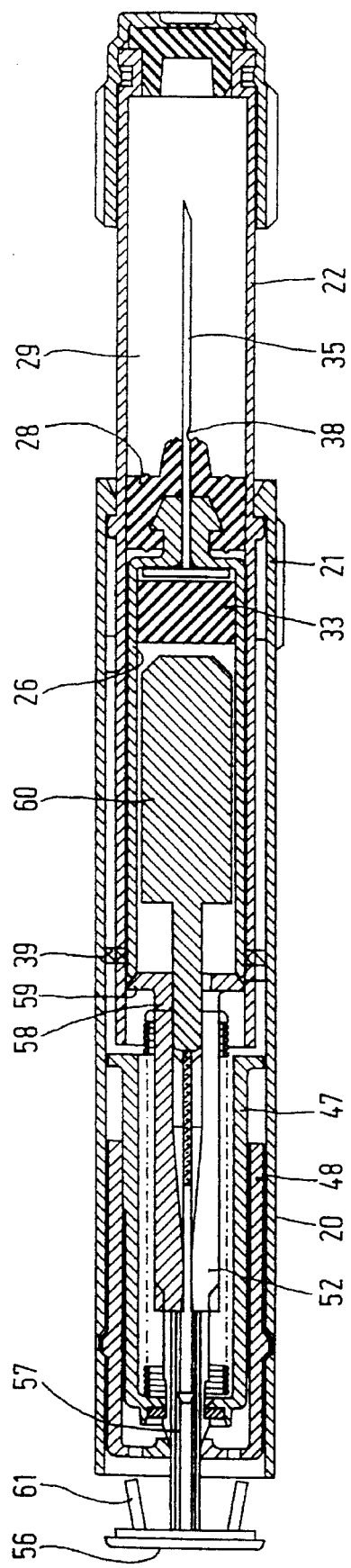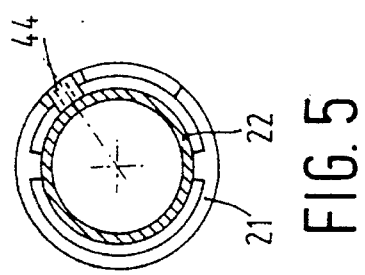
FIG. 4
FIG. 5

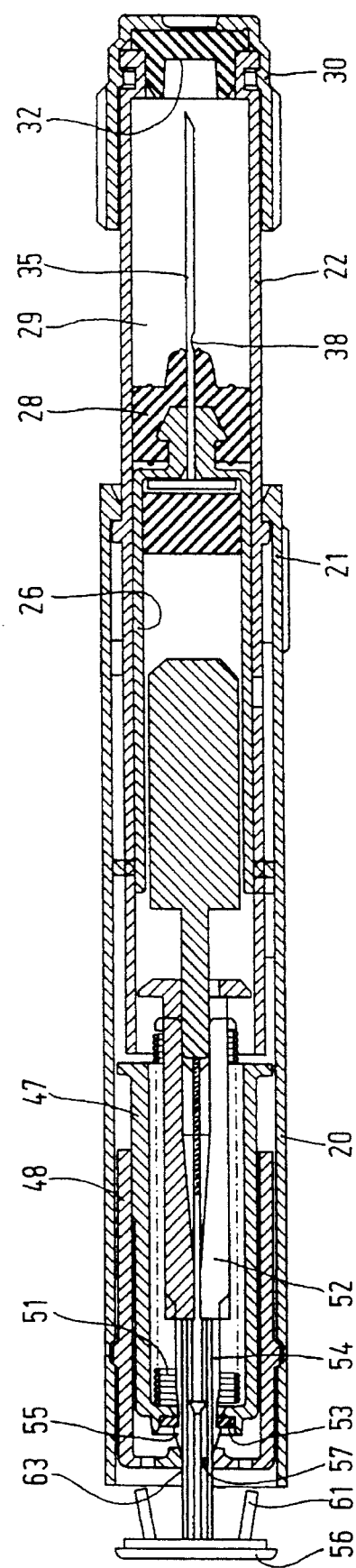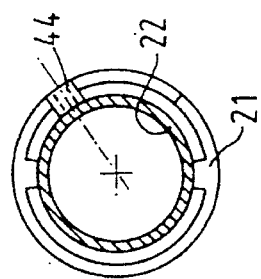
FIG. 7
FIG. 8

AUTOMATIC INJECTOR

The invention relates to an automatic injector, in which, prior to use, different substances which are not allowed to be in contact with each other for a long period of time, can be stored separately, one of said substances being a solid and another being or comprising a solvent for this solid, which solid can be injected as an injection liquid after dissolving it in said solvent.

Automatic injectors have been designed in particular for use by human beings who at a given instant, which is not known beforehand, have to administer an injection into their own body. These beings include, for example, soldiers after having been exposed to an enemy's battle gas, for example a nerve gas. It therefore will be obvious that automatic injectors must satisfy stringent requirements regarding their reliability in use. Such injectors are usually stored for many years at a time, and in addition, after having been handed over to the potential users, will be kept by said users for long periods of time under varying conditions; the proper operation of the injectors must be sufficiently ensured. In fact, at the critical instant the user's life may depend on the operation of the injector. Therefore, automatic injectors must satisfy stringent requirements as for their storage stability.

The administration of several medicaments or antidotes is often necessary in particular for military use, inter alia, because, as a matter of fact, nature and composition of the battle gas used by the enemy are not known beforehand and/or to achieve an effective therapy. Some medicaments, which are sufficient storage stable as solids, are not stable for the required long storage period after having been dissolved in a solvent to form a solution suitable for injection. An automatic injector in which a solid as such can be accommodated might provide a solution to the problem of storing these medicaments.

Such injectors are under development during the last years. Examples of such automatic injectors are described, for example, in European Patents 0219899 and 0245895, both in the name of Applicants, and in U.S. Pat. No. 4,755,169. In the last-mentioned patent publication an embodiment of an automatic injector is disclosed, having telescopically mounted containers, viz. an outer container accommodating a medicament and confined at its rearward end by a piston, and an inner container mounted within the outer container rearwardly of the piston and accommodating a liquid ingredient (FIG. 10–11 embodiment of U.S. Pat. No. 4,755,169). As a result of a first release of a stressed spring assembly, a needle pierces said piston to communicate the interiors of inner and outer containers, and the liquid ingredient flows to the medicament in the outer container. After this operation the spring has expanded axially to a small extent. After mixing the ingredients in the injector by shaking, the user can actuate the injector to effect a second release of the partly expanded spring in order to effect the actual injection.

The above known injector has various drawbacks. The injector is very complicated and includes, for example, two separate injection needles, one for communicating the interiors of the containers and a second for performing the actual injection, as well as two separate releasing assemblies, one for a first release of the stressed spring to a partial expansion thereof and a second one for a complete release of said spring. It will be obvious, that a very powerful spring is needed, to leave after the first release a spring power of at least approx. 120N, needed for driving the needle through the clothes into the muscle tissue.

In U.S. Pat. No. 5,041,088 an automatic injector is disclosed for the same above purpose, having two coaxially situated chambers separated by a thin impermeable membrane, said chambers containing different ingredients of a medicament. Through the rear chamber a cutting or piercing means (lance) extends, capable of cutting or piercing said membrane in order to communicate the interiors of the chambers. For this purpose the lance is mounted in a boring of a piston (plunger), slidably accommodated in the inner tube (liner). The disadvantages of such an automatic injector are evident. Because of the various complicated constructing parts, especially the sliding lance mounted in a boring of a piston, the injector is mechanically not reliable, certainly not after the required storage period of 5 years. The assemblage as well as the filling operation with the ingredients of the medicament under sterile conditions are very difficult. Further, the use of a highly vulnerable membrane to separate the chambers is very problematic and impedes the assemblage and filling operations even more. Last but not least, the lance as used for cutting or piercing the membrane extends at full length through the rear chamber, as a result of which an excessive amount of air, present in this chamber, will be co-injected.

The present invention relates more in particular to an automatic injector, in which, prior to use, different substances which are not allowed to be in contact with each other for a long period of time, can be stored separately, one of said substances being a solid and another being or comprising a solvent for this solid, which solid can be injected as an injection liquid after dissolving it in said solvent;

said injector comprising a discharge mechanism, a cartridge assembly, and a front cover, connected to a front portion of said cartridge assembly and provided at its front with a pierceable central area;

said cartridge assembly comprising:

a plurality of different substances, accommodated in separate compartments in said cartridge assembly, a hollow barrel which is open at its rear end and which comprises a substantially cylindrical portion, a means functioning as a piston, which is movable in said substantially cylindrical portion of the barrel, and a needle for injecting said injection liquid;

said discharge mechanism being connected in a cylindrical outer sleeve and being in operative relation to said piston; and said front cover being capable of rotational movement relative to said outer sleeve in order to allow the interior of the compartment accommodating the solid to communicate with the interior of the compartment accommodating the solvent for this solid, as a result of which the solid and the solvent can reach each other, so that the solvent can dissolve the solid and the injector is made ready for use.

Such an automatic injector is known from European Patent Application 0288443.

Although this injector can easily made ready for use by a simple rotational movement and looks rather reliable, it has still some serious disadvantages which makes it less attractive. The compartments are separated from each other by a vulnerable membrane exactly as in the previously-discussed patent publication. This membrane is welded at the front of the powder chamber, a less reliable construction. During the making-ready-for-use operation of this known injector, the powdered medicament in the powder chamber is sprayed into the liquid medicament as illustrated in FIG. 11B of said patent application. Then insufficient mixing and the presence of dead spaces, where undissolved powder may easily remain, are serious risks. In addition, the assemblage is very difficult due to the complicated construction.

It is the objective of the present invention to provide an automatic injector for the purpose as defined in the opening paragraph, which injector does not present the above disadvantages.

This objective can be achieved by means of an injector as defined above, viz.:

comprising a discharge mechanism, a cartridge assembly, and a front cover, connected to a front portion of said cartridge assembly and provided at its front with a pierceable central area;

said cartridge assembly comprising:

a plurality of different substances, accommodated in separate compartments in said cartridge assembly, a hollow barrel which is open at its rear end and which comprises a substantially cylindrical portion, a piston, which is movable in said substantially cylindrical portion of the barrel, and a needle for injecting said injection liquid;

said discharge mechanism being connected in a cylindrical outer sleeve and being in operative relation to said piston; and said front cover being capable of rotational movement relative to said outer sleeve in order to allow the interior of the compartment accommodating the solid to communicate with the interior of the compartment accommodating the solvent for this solid, as a result of which the solid and the solvent can reach each other, so that the solvent can dissolve the solid and the injector is made ready for use; which injector is characterized according to the present invention, in that:

said cartridge assembly comprises a cartridge container, to the front portion of which said front cover is connected and which slidably accommodates a cartridge, said cartridge comprising:

a hollow barrel having a backward portion with a cylindrical inner surface and a front portion, a pierceable stopper sealingly connected to the front portion of the barrel and constituting a compartment in front of said stopper for accommodating the solid (solid compartment), said compartment being bound at its rear by the front face of said stopper, at its lateral side by the inner wall of the front portion of the cartridge container and at its front by the pierceable central area of the front cover, said pierceable stopper being capable of axial movement in said cartridge container, a piston slidably accommodated in the backward portion of the barrel and constituting a compartment for liquid in said barrel, an injection needle longitudinally extending in said liquid compartment, said needle having a bearing at its proximal end, which bearing centers said proximal end in the barrel, said injection needle being provided with inlet openings, one near the bearing and another at a distance from the front face of the bearing exceeding the length of the pierceable stopper, and a means for centering the distal end of the needle in order to position the needle tip towards the pierceable stopper; wherein said rotational movement of the front cover relative to the outer sleeve causes a backward movement of the barrel in the cartridge container, the piston and the needle bearing thereon remaining in their places, as a result of which the injection needle pierces the pierceable stopper and allows the liquid in the barrel to reach the solid compartment through the needle.

The automatic injector of the present invention is composed of a relatively small number of constructive parts and can easily be assembled and filled under sterile conditions. The construction only allows the operation of the injector in predetermined steps, which promotes the safe functioning of the injector. Instead of a vulnerable membrane, the sealing between the two compartments is provided by a pierceable stopper, a solid and reliable construction. During the making-ready-for-use operation, the liquid sprays through the needle into the solid compartment so as to afford a complete and fast mixing with the solid.

The injector according to the present invention may also comprise two different liquids in the liquid compartment, separated from each other prior to use of the injector. Such an embodiment is particularly suitable for accommodating different liquid medicaments not compatible during the required long storage period. As a consequence, the injector of the invention is particularly flexible, because it may accommodate one and more than one liquid ingredient. A sealing member for separating the different liquids during storage of the injector may easily be realized by providing a separating stopper in the liquid compartment. During the operation for making the injector ready for use, the liquids at either side of said separating stopper can reach the solid compartment through the needle, if the needle is provided with suitably situated inlet openings. For this purpose, the inlet opening in the injection needle proximate to the needle tip, preferably a side opening in the wall of the needle cannula, should be situated so, that after making the injector ready for use, this opening is just in front of the front face of the pierceable stopper. It will therefore be obvious, that by the above expression "the length of the pierceable stopper" is meant: the distance between front face and rear face of the pierceable stopper, including the thickness of the front portion of the barrel and, in case a separating stopper is provided in the barrel, also including the length of said separating stopper.

Alternatively, in case the injector comprises two different liquids separated by a separating stopper, a by-pass means may be formed in the side-wall of the barrel, through which, during the making-ready-for-use operation, the liquids can reach each other and then, after mixing, can together flow through the needle to the solid compartment. Such a by-pass means in the barrel wall may be constructed in various manners, e.g. as described in detail in the above-mentioned European Patent 0219899. Such a by-pass means is preferably in the form of at least one slot or groove, recessed in the inner wall of the barrel, or at least one ridge, provided on the inner wall of said barrel, both extending in the longitudinal direction of the barrel. In the latter case, the separating stopper is deformed by contacting said ridge during the making-ready-for-use operation, by-passes for injection liquid being formed at either side of said ridge.

The solid, to be accommodated in the solid compartment, may be present in the form of an, optionally lyophilized, powder, a tablet, granules, crystals, pills and the like. The term "solid" should be interpreted widely and also includes a medicament which can be injected only after dilution with a diluent. Such medicaments may be accommodated in the injector in the form of pastes or concentrated solutions which cannot be injected as such. The needle then serves as a by-pass for the diluent. The terms "solid" and "solvent" for said solvent, as used in the specification and claims, should therefore be understood to include "medicament to be diluted before injection" and "diluent" for such a medicament.

The solvent for the solid, accommodated in the liquid compartment situated in the barrel, may conveniently comprise a medicament dissolved therein, provided such a medicament is compatible with the solvent during storage of the injector. As an example, when the liquid in the liquid compartment is substantially composed of a physiologically saline solution, this solution may comprise various medicaments, such as atropine, Diazepam™ and/or Avizafone™.

The needle bearing may be constructed as a separate disk-like needle base, to which the needle is connected with its proximal end, e.g. by shrinking, rivetting, gluing or welding. In an equally suitable embodiment the needle bearing is an integrated part of the needle, as described in U.S. Pat. No. 4,968,302, comprising at least one cannula winding at its proximal end, slidably fitting within the backward portion of the barrel.

In a suitable construction the front portion of the barrel may be narrowed to form a spout, in order to constitute a centering means for the distal end of the needle. The barrel is preferably manufactured from a rigid synthetic material, compatible with the liquid to be accommodated, preferably polypropylene of a pharmaceutical quality. The piston and the stoppers are manufactured from a suitable elastomer, preferably a rubber of a pharmaceutical quality.

In a preferred embodiment of the automatic injector of the invention, the outer sleeve has a prolonged front portion holding a backward portion of the cartridge container locked against forward movement, and the outer wall of the barrel comprises at least one outwardly extending projection, capable of sliding movement through at least one running groove, longitudinally recessed in the backward portion of the cartridge container, and with its free end bearing against at least one slide-way, longitudinally provided on the inner wall of the prolonged front portion of the outer sleeve, at least one of said running groove or said slideway being curved in an obliquely forward direction. Said at least one projection on the barrel wall in cooperation with said at least one running groove in the cartridge container and with said at least one slide-way on the outer sleeve's inner wall causes a backward movement of the cartridge in the cartridge container upon rotation of the front cover relative to the outer sleeve.

Preferably two outwardly extending projections are provided on the outer wall of the barrel. These projections may have the form of bosses, and may conveniently constitute, in case the barrel is manufactured from a synthetic material, integratedly formed parts of the barrel wall. Said slide-way provided on the inner wall of the outer sleeve may conveniently be formed by a groove or grooves in said inner wall. Alternatively, said slide-way may also conveniently be formed by composing said inner wall of two concentric portions, preferably integrated with each other, the inner portion being provided with recesses to constitute said slide-way on the outer portion. In this manner a slide-way is formed for conducting said projection on the barrel wall. The curved form of the running groove and/or of the slideway causes a conversion of a rotational movement into an axial movement (of the cartridge).

In a very suitable embodiment, both said at least one running groove and said at least one slide-way are curved, said curves forming acute angles with the longitudinal axis of the injector at opposite sides of this axis. It has been found, that such-formed running groove(s) and slide way(s) improve their mutual operative relation during the operation of making the injector ready for use. As a matter of fact, by curving both the running groove(s) and the slide way(s) under mutually opposite angles with regard to the longitudinal axis, a greater rotational movement of the front cover relative to the outer sleeve is needed for accomplishing the required full axial movement of the cartridge in the cartridge container. As a result, the operation of making the injector ready for use costs less effort and is therefore facilitated.

In a further preferred embodiment of the injector of the invention, the outer sleeve at its front is provided with an abutment for an outwardly extending stop boss provided on the outer wall of the cartridge container, to limit rotational movement of the cartridge container relative to the outer sleeve. In addition, rotational movement of the front cover relative to the outer sleeve in the reverse direction, after the injector has been made ready for use, is prevented. After the-ready-for-use operation has been completed, the rear face of the barrel's front portion, covered by the pierceable stopper, bears against the front face of the needle bearing, the rear face of said bearing bears against the front face of the piston, and the liquid has completely passed on into the solid compartment; then a slightly reduced pressure is present in said solid compartment. Due to this decompression, the barrel slightly moves forward in the cartridge container, in which position said at least one projection on the barrel wall is retained by an at least one appropriate abutment provided on the inner wall of the outer sleeve and in this manner rotational movement of the barrel in the reverse direction is prevented. This is also a good indication that the injector is ready for use.

After the injector has been made ready for use, it can be actuated to administer an injection. To avoid premature actuation of the injector, i.e., actuation before the operation for making the injector ready for use has been completed, the injector of the present invention is preferably provided with a suitable safety device. Therefore, in a preferred embodiment, the injector of the invention is constructed in such a manner, that the discharge mechanism comprises an inner pistol sleeve which is open at its front , a plunger which is movable in the inner pistol sleeve, a coil spring which acts on said plunger and tries to move the same out of the front of the inner pistol sleeve outwards, a locking device which cooperates with said plunger so as to prevent undesired forward movement thereof, and a safety member to block unintentional unlocking of the locking device, said safety member comprising a circular disk, fitting within the rear edge of the cylindrical outer sleeve, and centrally provided with an axially extending stem, said stem extending through said plunger and bearing with its free end against the rear face of a rod-like member, that protrudes from the front of said plunger and terminates at its front in an outwardly extending flange fitting within the cartridge container, the distance between said flange and the rear edge of the barrel wall being dimensioned such that the backward movement of the barrel in the cartridge container during the making ready for use operation pushes the safety member backwards so that the disk comes outside the rear edge of the outer sleeve.

In the above preferred construction, the safety member can only be removed manually after the making-ready-for-use operation has been completed. As a matter of fact, in this position the disk of the safety member protrudes backwards from the injector and can be gripped with the fingers. After removal of the safety member, the locking device is unlocked and the injector can be actuated, exactly as described in the above European Patent 0245895. At a glance it can be observed that the disk of the safety member protrudes backwards from the injector, giving a clear indication that the injector is ready for use. To avoid that the safety member may be pushed back in its original position after the making-ready-for-use operation, the injector of the invention is conveniently be designed in such a manner, that said discharge mechanism is connected in the cylindrical outer sleeve by means of an outer pistol sleeve within which the inner pistol sleeve can be moved telescopically, and that the disk of the safety member at the side of the stem is provided with at least two rod-shaped resilient elements (barbs), which elements form acute angles with the longitudinal axis of the injector in assembled condition and correspond to apertures recessed in the rear wall of the outer pistol sleeve. The rod-shaped resilient members, positioned on the inner side of the disk of the safety member, bent slightly outwards after the disk has pushed backwards, and so prevent replacement of the safety member in its original position.

The invention will now be described in greater detail with reference to a preferred embodiment which is shown in the drawings, in which:

FIGS. 4, 5 and 6 show the same injector as presented in FIGS. 1, 2 and 3, respectively, after completion of the operation for making the injector ready for use;

FIGS. 7, 8 and 9 illustrate the situation, at which the FIGS. 1–6 injector is ready for use.

Figure 1:
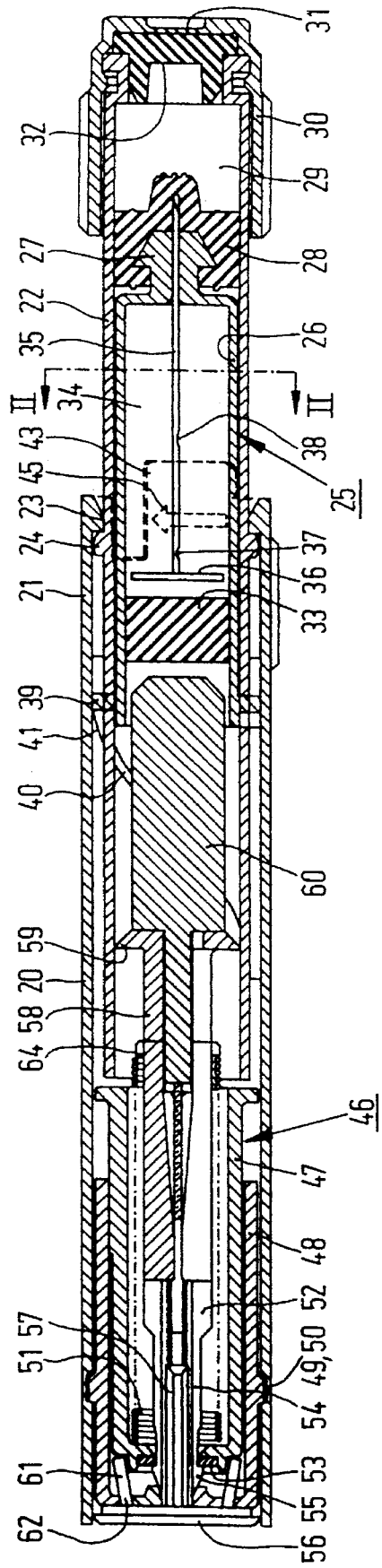
FIG. 1 is a longitudinal sectional view of an injector according to the invention, in the condition in which the injector can be transported and stored.
Figure 2:
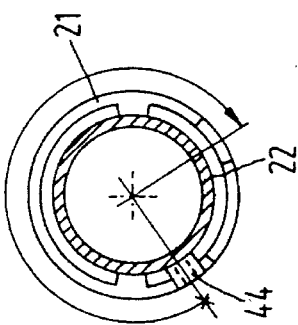
FIG. 2 is a cross-sectional view through the injector's cartridge container as shown in FIG. 1, taken on the line II—II, viewed in the backward direction.
Figure 3:
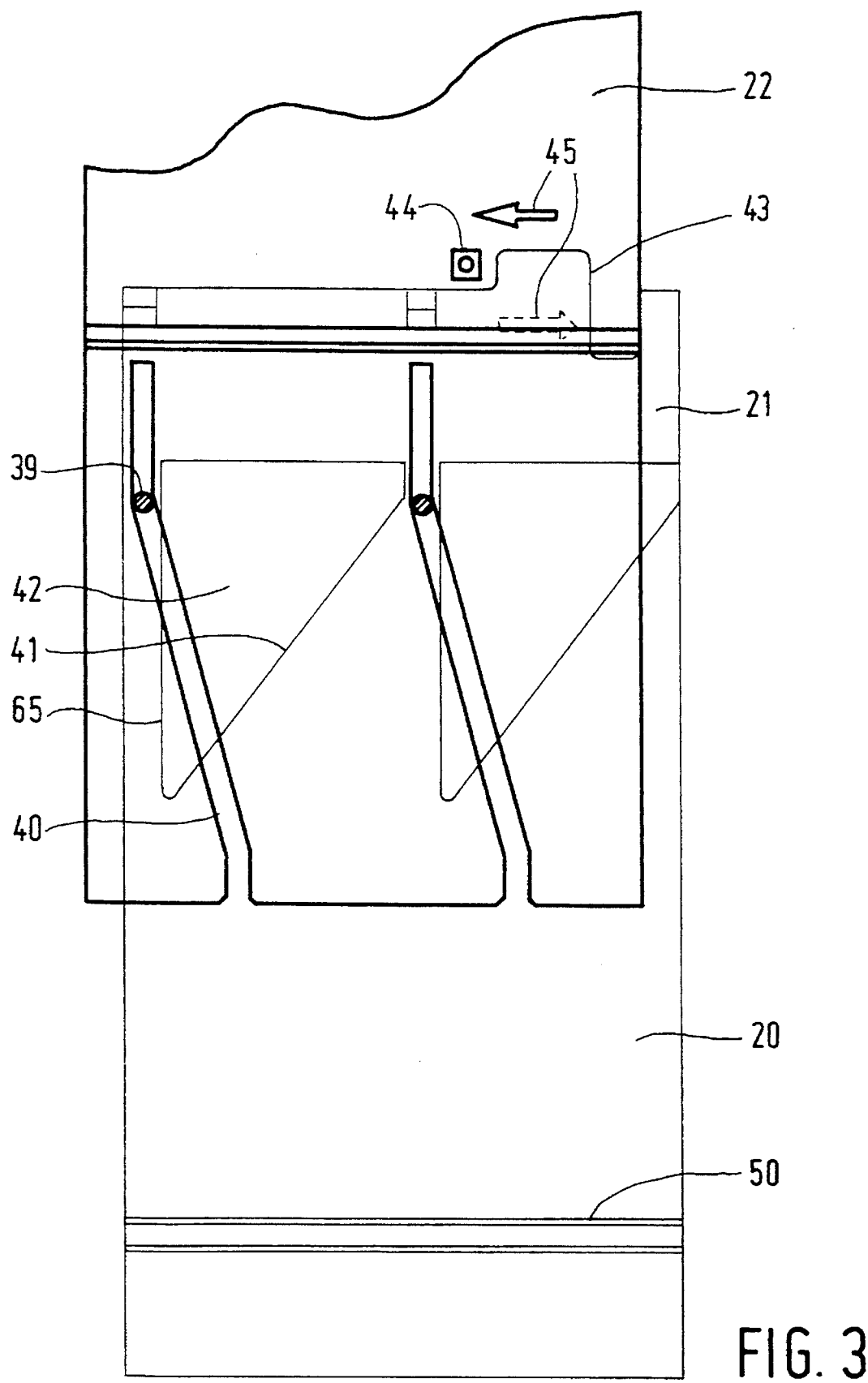
FIG. 3 is a picture of the assembly of outer sleeve and cartridge container of the FIG. 1 injector, shown in a position opened in the longitudinal direction and projected in a plane.

The automatic injector shown in FIGS. 1–3 comprises an outer sleeve 20, having a prolongued front portion 21 holding a cartridge container 22 locked against forward movement by means of two diametrical inward projections 23 at its front; an annular ridge 24 outwardly provided on the outer wall of the cartridge container engages behind said projections 23. In the cartridge container is slidably accommodated a cartridge 25, comprising a hollow barrel 26 with a narrowed front portion 27, serving as a centering means for the injection needle. The front portion 27 of the barrel is sealingly covered by a pierceable stopper 28, constituting a compartment 29 in the cartridge container for accommodating a solid. A front cover 30 is connected to a front portion of the cartridge container, which front cover has a central aperture or may be provided, if so desired, with a thin-walled central portion 31 for tamper-evidence.

Said thin-walled central portion bears against a rubber sealing stopper 32, sealing the foremost end of the cartridge container. Said sealing stopper together with the thin-walled central portion of the front cover, if present, form a central area pierceable by the injection needle upon use of the injector. A piston 33, capable of sliding movement in the rear portion of the barrel, constitutes a compartment 34 for liquid in the barrel. An injection needle 35 extends longitudinally in this liquid compartment, having a bearing 36 in the form of a disk at its proximal end. The injection needle has two inlet openings 37 and 38, both provided as side-openings in the cannula wall.

The outer wall of the barrel 26 is diametrically provided with two outwardly extending projections 39, slidably movable through two running grooves 40, diametrically recessed in the backward portion of the cartridge container. The free ends of these projections bear against two slide-ways 41, diametrically provided on the inner wall of the outer sleeve.

As is visualized in FIG. 3, where the cartridge container 22 is exposed on top of the inner wall of the outer sleeve 20, said inner wall is provided with two bearing areas 42, having triangular circumferences in planar projection. These bearing areas constitute with their obliquely backwards directed raised sides 41 slide-ways for the projections. The bearing areas 42 further present axially backwards extending raised sides 65. The front of the outer sleeve 20 is provided with an abutment 43 for an outwardly extending stop boss 44 on the outer wall of the cartridge container. Further two arrows 45 are oppositely directed provided, on the outer wall of the cartridge container and on the outer wall of the outer sleeve, respectively, to indicate the direction of rotational movement of said cartridge container relative to the outer sleeve upon making the injector ready for use.

The discharge mechanism 46 comprises an inner pistol sleeve 47, slidably accommodated in an outer pistol sleeve 48, connected in the outer sleeve 20 with an annular ridge (49)—circumferential groove (50) construction. A coil spring 51 is provided in the inner pistol sleeve and acts on an out-turned flanged head 64 of a plunger 52, trying to move said plunger out of the front of the inner pistol sleeve outwards. A rigid washer 53, provided on the rear central aperture of the inner pistol sleeve, prevents undesired forward movement of the plunger by constituting a bearing for a plurality of backwards extending, slightly resilient detent arms 54 of said plunger, terminating in conical detent heads 55. A safety member, comprising a circular disk 56, fitting within the rear edge of the cylindrical outer sleeve 20, is centrally provided with an axially extending stem 57, terminating in a plurality of legs. This stem extends through said detend arms of the plunger, preventing unintentional inward bending of these detent arms, and bears with the free ends of its legs against the rear face of a rod-like member 58, that protrudes from the front of said plunger and terminates at its front in an outwardly extending flange 59, fitting within the cartridge container 22. Between the front face of said flange and the rear face of the piston 33 a spacing member 60 is arranged for bridging the distance between said red-like member and the piston. The safety member comprises in addition two rod-shaped resilient elements 61, thus provided on the disk of the safety member, that in assembled condition they form an acute angle with the longitudinal axis of the injector. These elements can be inserted into two corresponding apertures 62 recessed in the rear wall of the outer pistol sleeve 48.

Figure 6:
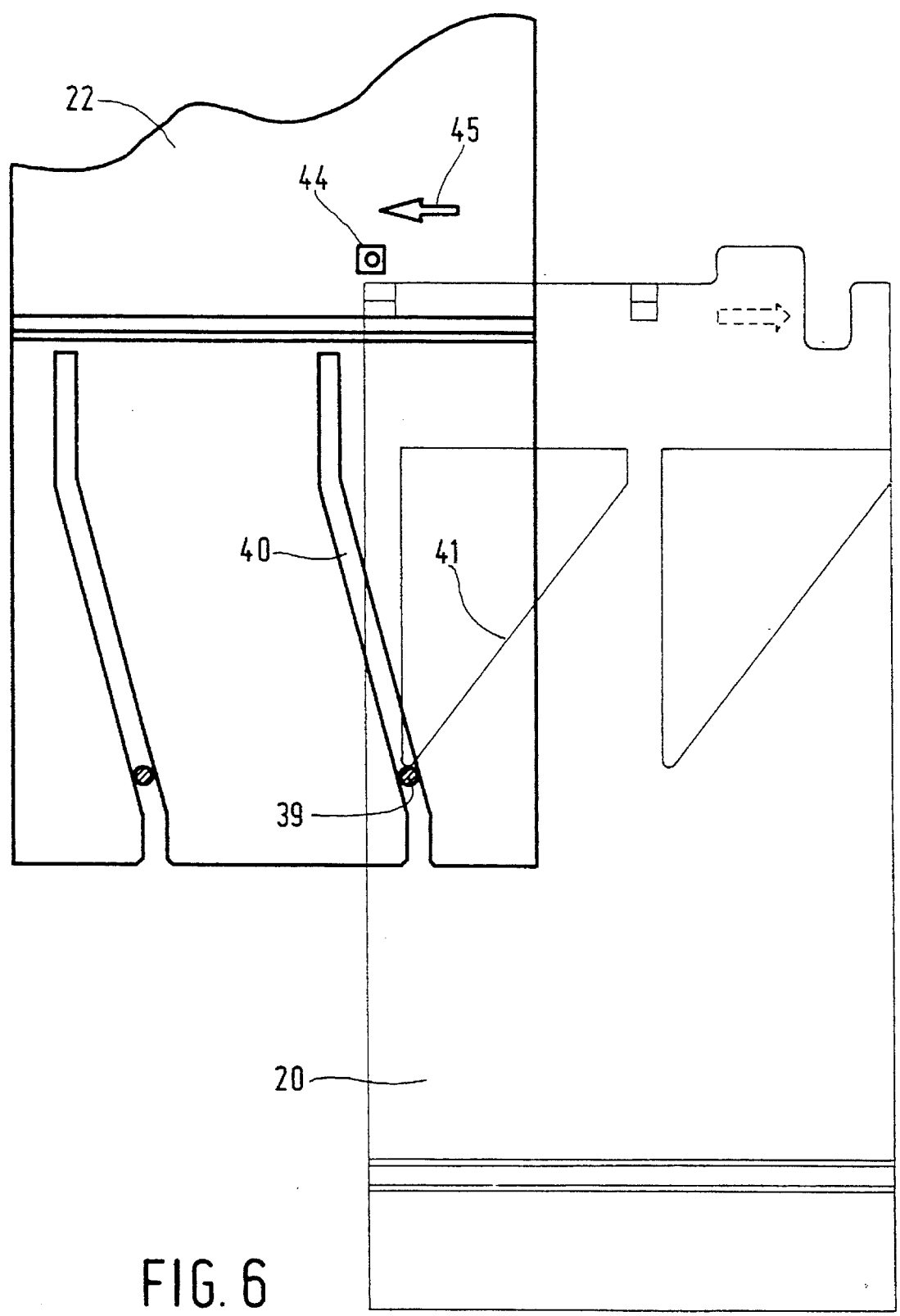

The operation for making the injector ready for use is visualized in FIGS. 4–6. The curved shapes both of the running grooves recessed in the cartridge container and of the slide-ways on the inner wall of the outer sleeve influence the "thread" of the rotational movement. As indicated with an arrow in FIG. 2, a rotation of approx. 270° between cartridge container and outer sleeve results in the FIG. 4 situation, where the operation for making the injector ready for use has been completed. During this operation, the projections 39 on the barrel wall slide through the running grooves 40 in the cartridge container and along the slide-ways 41 on the inner wall of the outer sleeve's front portion 21; this is visualized in FIG. 6 (compare also FIG. 3). During this rotational movement, the barrel plus pierceable stopper move backwards in the cartridge container. The piston 33 and the needle 35 bearing on the piston remain in their places, because the piston is locked against backward movement via spacing member 60, rod-like member 58, stem 57 of the safety member and pistol sleeves 47 and 48 in the outer sleeve 20. As a result of this rotational movement of the front cover plus connected cartridge container relative to the outer sleeve, the injection needle pierces the pierceable stopper 28 and allows the injection liquid in the barrel to reach the solid in the solid compartment 29 through the needle: situation of FIG. 4. The foremost side-opening 38 in the needle cannula is now situated just in front of the front face of the pierceable stopper 28. During the last stage of the making-ready-for-use operation the rear edge of the backwards shifting barrel wall contacts the front face of the flange 59 of the rod-like member 58, pushing this member and simultaneously therewith the safety member backwards over a pre-determined distance, because the stem 57 of the safety member bears with its free end against the rear face of the rod-like member 58. It should be emphasized, that the rod-like member 58 and the plunger 52 are so constructed and assembled, that they do not interfere their mutually independent axial movements. The disk 56 of the safety member has now come outside the rear edge of the outer sleeve. In this position of the safety member the resilient elements 61 are directed in a slightly outwardly-bent position, so that replacement of the safety member in its original position is prevented.

Figure 9:
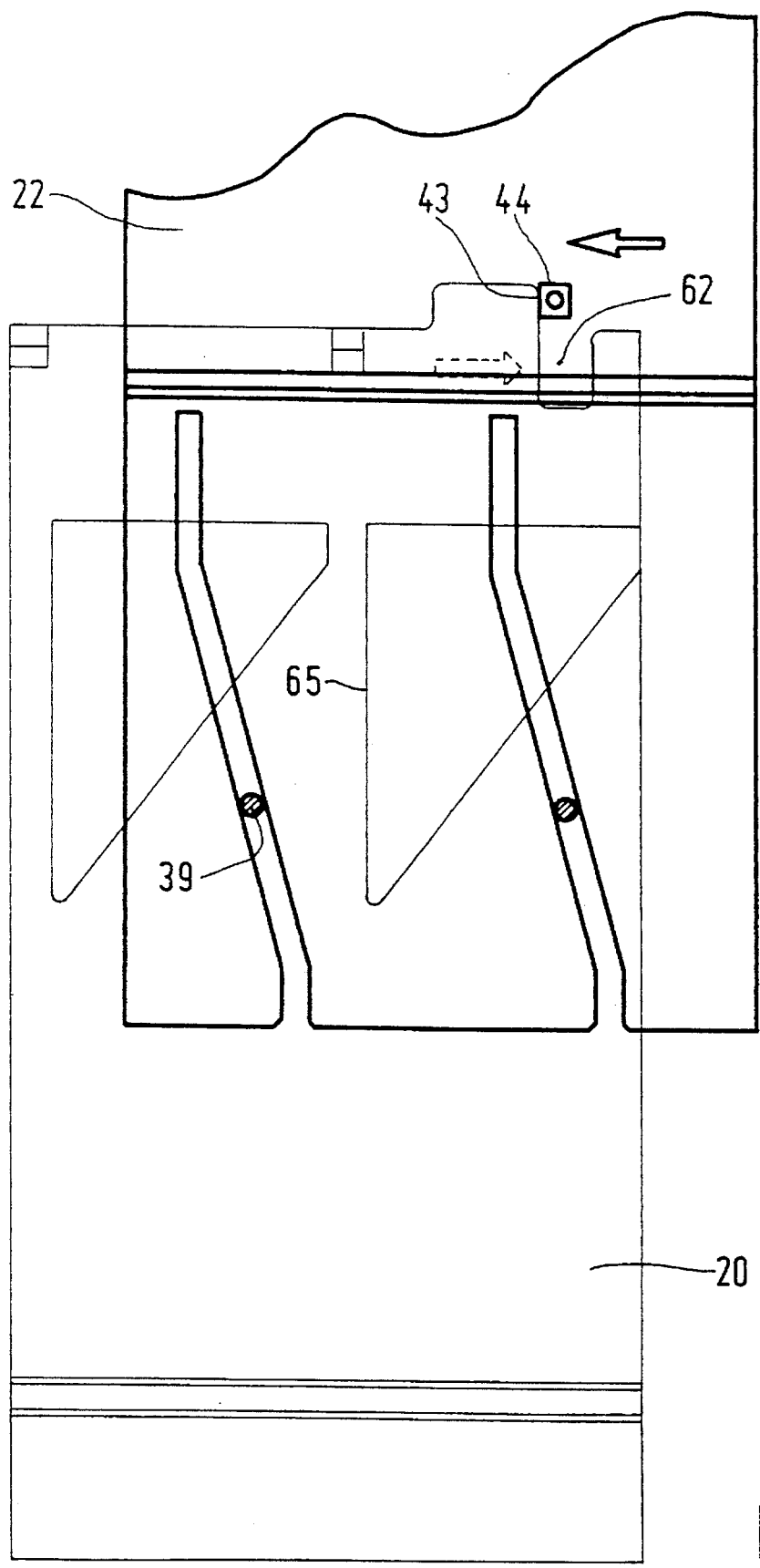
Figure 10:
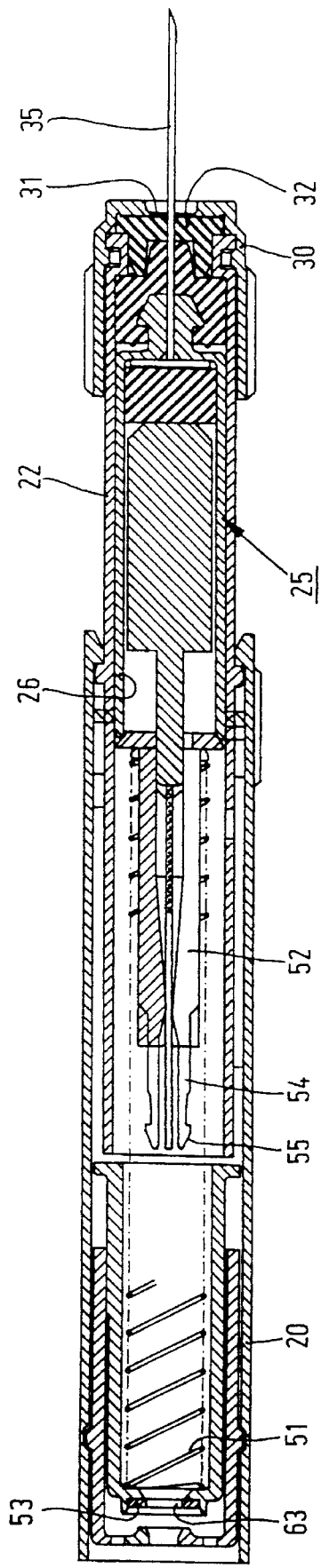
FIG. 10 illustrates the situation after which the same injector has been actuated and the injection liquid has been expelled.

After the manual operation for making the injector ready for use has been completed, the barrel slightly moves forward in the cartridge container as a result of a slightly reduced pressure originated in the cartridge container in front of the pierceable stopper (compartment 29, now accommodating solid+liquid). This position is visualized in FIGS. 7–9. As can be observed in FIG. 9, stop boss 44 in cooperation with abutment 43 prevents further rotational movement of the cartridge container relative to the outer sleeve. Rotational movement in the reverse direction is now prevented by projections 39, abutting against raised sides 65. The indent 62 at the front of the outer sleeve allows receipt of the stop boss when upon actuation of the injector (see further) the cartridge container is pushed backwards in the outer sleeve. After shaking the injector to dissolve the solid into the liquid, the injector is now ready for use. The injector can now be actuated in the same manner as the automatic injector described in the above European Patent 0245895. To administer an injection, the safety member is first removed by exerting a rearwardly directed force on the disk 56, as a result of which the stem 57 is pulled away from between the resilient detent arms 54 of the plunger. By firmly pressing the nose of the injector, i.e. the front face of the front cover 30, against the body at the area where the injection is to be administered, the locking mechanism of the injector is unlocked. This unlocking operation takes place in that the cartridge container pushes the inner pistol sleeve backwards relative to the outer pistol sleeve, as a result of which the resilient detent arms 54 bent inwards because of the entrance of the conical detent heads 55 into the central aperture 63 of the outer pistol sleeve 48. Simultaneously the detent heads are released from their bearing, viz. from washer 53, and the plunger is pushed forwards under the influence of the relaxing coil spring 51. After actuation of the injector, the cartridge moves forwards in the cartridge container, the needle pierces the sealing stopper 32 and penetrates into the body. Upon penetrating the body, the injection liquid in compartment 29 leaves the injector under the influence of the same spring through the needle, opening 38 allowing the injection liquid to enter the needle cannula. After expelling the injection liquid from the injector, the situation is reached as shown in FIG. 10. It will be obvious, that the inner wall of the front of the barrel and the front face of the piston, as well as the front face of the pierceable stopper and the rear face of the nose portion, i.e. of the front of the cartridge container plus the sealing stopper, are preferably approximately complementary to avoid substantial loss of injection liquid, remaining in the injector after its use.

I claim:

1. An automatic injector, in which, prior to use, different substances which are not allowed to be in contact with each other for a long period of time, can be stored separately, one of said substances being a solid and another being or comprising a solvent for this solid, which solid can be injected as an injection liquid after dissolving it in said solvent; said injector comprising a discharge mechanism, a cartridge assembly, and a front cover, connected to a front portion of said cartridge assembly and provided at its front with a pierceable central area;

said cartridge assembly comprising:
a plurality of different substances, accommodated in separate compartments in said cartridge assembly,
a hollow barrel which is open at its rear end and which comprises a substantially cylindrical portion,
a piston, which is movable in said substantially cylindrical portion of the barrel, and
a needle for injecting said injection liquid;

said discharge mechanism being connected in a cylindrical outer sleeve and being in operative relation to said piston; and said front cover being capable of rotational movement relative to said outer sleeve in order to allow the interior of the compartment accommodating the solid to communicate with the interior of the compartment accommodating the solvent for this solid, as a result of which the solid and the solvent can reach each other, so that the solvent can dissolve the solid and the injector is made ready for use;

said injector being characterized in that:

said cartridge assembly comprises a cartridge container, to the front portion of which said front cover is connected and which slidably accommodates a cartridge, said cartridge comprising:
a hollow barrel having a backward portion with a cylindrical inner surface and a front portion,
a pierceable stopper sealingly connected to the front portion of the barrel and constituting a compartment in front of said stopper for accommodating the solid (solid compartment), said compartment being bound at its rear by the front face of said stopper, at its lateral side by the inner wall of the front portion of the cartridge container and at its front by the pierceable central area of the front cover, said pierceable stopper being capable of axial movement in said cartridge container,
a piston slidably accommodated in the backward portion of the barrel and constituting a compartment for liquid in said barrel,
an injection needle longitudinally extending in said liquid compartment, said needle having a bearing at its proximal end, which bearing centers said proximal end in the barrel, said injection needle being provided with inlet openings, one near the bearing and another at a distance from the front face of the bearing exceeding the length of the pierceable stopper, and
a means for centering the distal end of the needle in order to position the needle tip towards the pierceable stopper;

wherein said rotational movement of the front cover relative to the outer sleeve causes a backward movement of the barrel in the cartridge container, the piston and the needle bearing thereon remaining in their places, as a result of which the injection needle pierces the pierceable stopper and allows the liquid in the barrel to reach the solid compartment through the needle, said injection needle is accommodated in the barrel in an unfixed manner to allow relative longitudinal movement between the injection needle and the barrel.

2. An injector according to claim 1, characterized in that the outer sleeve has a prolonged front portion holding a backward portion of the cartridge container locked against forward movement, and that the outer wall of the barrel comprises at least one outwardly extending projection, capable of sliding movement through at least one running groove, longitudinally recessed in the backward portion of the cartridge container, and with its free end bearing against at least one slide-way, longitudinally provided on the inner wall of the prolonged front portion of the outer sleeve, at least one of said running groove or said slideway being curved in an obliquely forward direction, wherein said at least one projection on the barrel wall in cooperation with said at least one running groove in the cartridge container and with said at least one slide-way on the outer sleeve's inner wall causes a backward movement of the cartridge in the cartridge container upon rotation of the front cover relative to the outer sleeve.

3. An injector according to claim 2, characterized in that the discharge mechanism comprises an inner pistol sleeve which is open at its front, a plunger which is movable in the inner pistol sleeve, a coil spring which acts on said plunger and tries to move the same out of the front of the inner pistol sleeve outwards, a locking device which cooperates with said plunger so as to prevent undesired forward movement thereof, and a safety member to block unintentional unlocking of the locking device, said safety member comprising a circular disk, fitting within the rear edge of the cylindrical outer sleeve, and centrally provided with an axially extending stem, said stem extending through said plunger and bearing with its free end against the rear face of a rod-like member, that protrudes from the front of said plunger and terminates at its front in an outwardly extending flange fitting within the cartridge container, the distance between said flange and the rear edge of the barrel wall being dimensioned such that the backward movement of the barrel in the cartridge container during the making ready for use operation pushes the safety member backwards so that the disk comes outside the rear edge of the outer sleeve.

4. An injector according to claim 3, characterized in that said discharge mechanism is connected in the cylindrical outer sleeve by means of an outer pistol sleeve within which the inner pistol sleeve can be moved telescopically, and that the disk of the safety member at the side of the stem is provided with at least two rod-shaped resilient elements (barbs), which elements form acute angles with the longitudinal axis of the injector in assembled condition and correspond to apertures recessed in the rear wall of the outer pistol sleeve.

5. An injector according to claim 2, characterized in that both said at least one running groove and said at least one slide-way are curved, said curves forming acute angles with the longitudinal axis of the injector at opposite sides of this axis.

6. An injector according to claim 5, characterized in that the outer sleeve at its front is provided with an abutment for an outwardly extending stop boss provided on the outer wall of the cartridge container, to limit rotational movement of the cartridge container relative to the outer sleeve.

7. An injector according to claim 6, characterized in that the discharge mechanism comprises an inner pistol sleeve which is open at its front, a plunger which is movable in the inner pistol sleeve, a coil spring which acts on said plunger and tries to move the same out of the front of the inner pistol sleeve outwards, a locking device which cooperates with said plunger so as to prevent undesired forward movement thereof, and a safety member to block unintentional unlocking of the locking device, said safety member comprising a circular disk, fitting within the rear edge of the cylindrical outer sleeve, and centrally provided with an axially extending stem, said stem extending through said plunger and bearing with its free end against the rear face of a rod-like member, that protrudes from the front of said plunger and terminates at its front in an outwardly extending flange fitting within the cartridge container, the distance between said flange and the rear edge of the barrel wall being dimensioned such that the backward movement of the barrel in the cartridge container during the making ready for use operation pushes the safety member backwards so that the disk comes outside the rear edge of the outer sleeve.

8. An injector according to claim 7, characterized in that said discharge mechanism is connected in the cylindrical outer sleeve by means of an outer pistol sleeve within which the inner pistol sleeve can be moved telescopically, and that the disk of the safety member at the side of the stem is provided with at least two rod-shaped resilient elements (barbs), which elements form acute angles with the longitudinal axis of the injector in assembled condition and correspond to apertures recessed in the rear wall of the outer pistol sleeve.

9. An injector according to claim 5, characterized in that the discharge mechanism comprises an inner pistol sleeve which is open at its front, a plunger which is movable in the inner pistol sleeve, a coil spring which acts on said plunger and tries to move the same out of the front of the inner pistol sleeve outwards, a locking device which cooperates with said plunger so as to prevent undesired forward movement thereof, and a safety member to block unintentional unlocking of the locking device, said safety member comprising a circular disk, fitting within the rear edge of the cylindrical outer sleeve, and centrally provided with an axially extending stem, said stem extending through said plunger and bearing with its free end against the rear face of a rod-like member, that protrudes from the front of said plunger and terminates at its front in an outwardly extending flange fitting within the cartridge container, the distance between said flange and the rear edge of the barrel wall being dimensioned such that the backward movement of the barrel in the cartridge container during the making ready for use operation pushes the safety member backwards so that the disk comes outside the rear edge of the outer sleeve.

10. An injector according to claim 9, characterized in that said discharge mechanism is connected in the cylindrical outer sleeve by means of an outer pistol sleeve within which the inner pistol sleeve can be moved telescopically, and that the disk of the safety member at the side of the stem is provided with at least two rod-shaped resilient elements (barbs), which elements form acute angles with the longitudinal axis of the injector in assembled condition and correspond to apertures recessed in the rear wall of the outer pistol sleeve.

11. An injector according to claim 1, characterized in that the discharge mechanism comprises an inner pistol sleeve which is open at its front, a plunger which is movable in the inner pistol sleeve, a coil spring which acts on said plunger and tries to move the same out of the front of the inner pistol sleeve outwards, a locking device which cooperates with said plunger so as to prevent undesired forward movement thereof, and a safety member to block unintentional unlocking of the locking device, said safety member comprising a circular disk, fitting within the rear edge of the cylindrical outer sleeve, and centrally provided with an axially extending stem, said stem extending through said plunger and bearing with its free end against the rear face of a rod-like member, that protrudes from the front of said plunger and terminates at its front in an outwardly extending flange fitting within the cartridge container, the distance between said flange and the rear edge of the barrel wall being dimensioned such that the backward movement of the barrel in the cartridge container during the making ready for use operation pushes the safety member backwards so that the disk comes outside the rear edge of the outer sleeve.

12. An injector according to claim 11, characterized in that said discharge mechanism is connected in the cylindrical outer sleeve by means of an outer pistol sleeve within which the inner pistol sleeve can be moved telescopically, and that the disk of the safety member at the side of the stem is provided with at least two rod-shaped resilient elements (barbs), which elements form acute angles with the longitudinal axis of the injector in assembled condition and correspond to apertures recessed in the rear wall of the outer pistol sleeve.

* * * * *